United States Patent
Shin

(12) 
(10) Patent No.: US 6,224,537 B1
(45) Date of Patent: May 1, 2001

(54) GOLF BAG AND GOLF BAG STRAP WITH MAGNETIC MATERIAL AND METHOD

(76) Inventor: Brian B. Shin, 2500 White Rd., Irvine, CA (US) 92714

( * ) Notice: Subject to any disclaimer, the term of this patent is extended or adjusted under 35 U.S.C. 154(b) by 0 days.

(21) Appl. No.: 09/334,752

(22) Filed: Jun. 16, 1999

(51) Int. Cl.[7] .................................................. A61N 2/08
(52) U.S. Cl. .............................................. 600/9; 206/315.3
(58) Field of Search ...................... 600/9–15; 206/315.3

(56) References Cited

U.S. PATENT DOCUMENTS

| | | | |
|---|---|---|---|
| 4,182,470 | * 1/1980 | Atkinson | 224/183 |
| 5,038,984 | * 8/1991 | Izzo | 224/643 |
| 5,707,333 | * 1/1998 | Bakst | 600/9 |
| 5,832,879 | * 11/1998 | Pitzen | 119/858 |
| 5,979,727 | * 11/1999 | Steurer | 224/645 |

* cited by examiner

*Primary Examiner*—Samuel G. Gilbert
(74) *Attorney, Agent, or Firm*—John J. Connors; Connors & Associates

(57) ABSTRACT

A golf bag comprises a bag body including a sidewall and having cavity therein adapted to hold golf clubs, and a shoulder strap connected to the sidewall and adapted to be draped over a shoulder of a user. Magnetic material is attached to the shoulder strap or the sidewall or both. It is positioned next to the area of the user's body experiencing pain as the golf bag is carried and assists in alleviating this pain.

11 Claims, 1 Drawing Sheet

GOLF BAG AND GOLF BAG STRAP WITH MAGNETIC MATERIAL AND METHOD

BACKGROUND OF THE INVENTION

Magnets, for example, strips of magnetic material are believed to provide therapeutic benefits when placed next to the surface of the skin of a user. The magnetic material helps to increase blood circulation, reduce inflammation, and increase oxygen in body areas experiencing pain. The magnetic material need not be in direct contact with the skin of the user, but should be overlying the area of the user's body that is experiencing pain and close enough so that the magnetic field penetrates the user's body. Typically, a strip of cloth containing the magnetic material is wrapped around the arm or leg of a user overlying the area of the body that is experiencing some pain. The clothing of the user maybe sandwiched between the skin of the user and strip of cloth.

SUMMARY OF THE INVENTION

This invention has several features, no single one of which is solely responsible for its desirable attributes. Without limiting the scope of this invention as expressed by the claims that follow, its more prominent features will now be discussed briefly. After considering this discussion, and particularly after reading the section entitled, "DETAILED DESCRIPTION OF THE PREFERRED EMBODIMENTS," one will understand how the features of this invention provide its benefits, which include, but are not limited to, treating pain while carrying a golf bag.

The first feature of the golf bag of this invention is that it includes magnetic material positioned through it at various locations. The magnetic material preferably is a flexible strip. The golf bag has a cavity therein adapted to hold golf clubs.

The second feature is that it includes a bag body with a sidewall, and preferably, there is a shoulder strap connected to the sidewall. The shoulder strap is adapted to be draped over a shoulder of a user. Preferably, the magnetic material is attached to the sidewall or the shoulder strap or both.

The third feature is that the shoulder strap may be either a single strap or dual loop strap. The dual loop strap has a pair of loops and a back pad that is positioned next to the back of a user when the user carries the golf bag with the shoulder strap draped over both shoulders. In a preferred embodiment the back pad includes the magnetic material.

The fourth feature is that this invention also comprises a strap adapted to be attached to a golf bag. This strap includes an elongated member having connector members at opposed ends thereof. These connectors may be any suitable fasteners such as, for example, clips, hooks, buckles, etc. that may be attached and detached to the sidewall of the bag. The magnetic material is attached to the elongated member and positioned thereon to make contact with the body of a person carrying a golf bag by draping over the person's shoulder the elongated member when attached to the golf bag.

This invention also includes a method of treating pain while playing golf. This method comprises carrying a golf bag with magnetic material included in a portion of the golf bag that is positioned next to the area of the user's body experiencing pain as the golf bag is carried. The portion of the golf bag including the magnetic material may be a strap draped over the shoulder. When the shoulder strap has a pair of loops and a back pad that is positioned next to the back of a user as the user carries the golf bag with the shoulder strap draped over both shoulders, the back pad includes the magnetic material. The portion of the golf bag including the magnetic material may also be a sidewall of the golf bag making contact with the user's back as the golf back is carried. The sidewall preferably includes a back pad that is positioned next to the back of a user as the user carries the golf bag. In such a case, the back pad includes the magnetic material.

DESCRIPTION OF THE DRAWING

The preferred embodiment of this invention, illustrating all its features, will now be discussed in detail. This embodiment depicts the novel and non-obvious golf bag and method of this invention as shown in the accompanying drawing, which is for illustrative purposes only. This drawing includes the following figures (FIGS.), with like numerals indicating like parts.

DETAILED DESCRIPTION OF THE PREFERRED EMBODIMENTS

Figure 1:
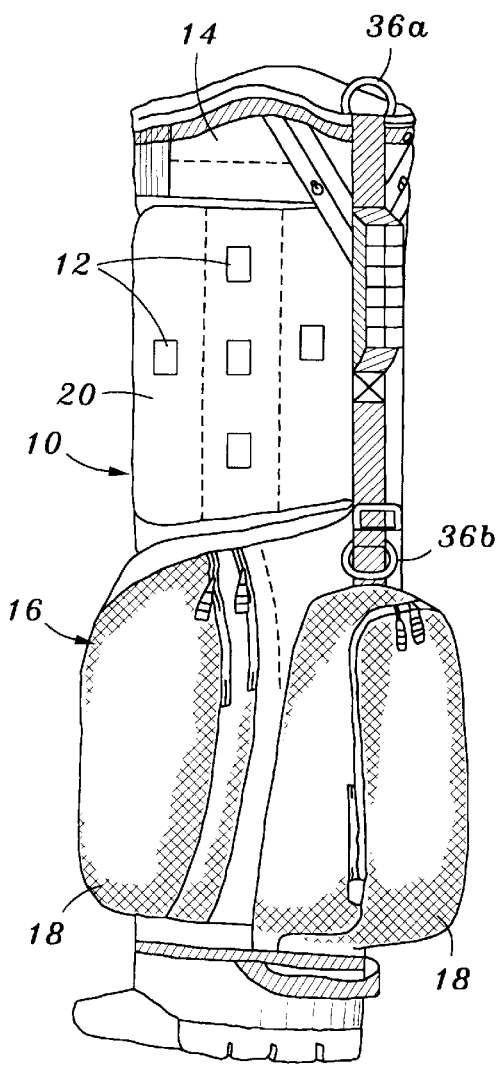
FIG. 1 is a perspective view of a golf bag having magnetic material attached to its sidewall.

FIG. 1 depicts a golf bag 10 with magnetic strips 12 attached to the sidewall 14 of the bag. This bag 10 is of convention design. It has a bag body 16 including the sidewall 14 with pockets 18 therein and a back pad 20 that rests against the lower back of the user when the bag is being carried by draping a strap (not shown) attached to the bag body 16 over the user's shoulder. In the preferred embodiment, the back pad 20 includes the magnetic strips 12. Five such strips 12 are employed and they are arranged in a cross configuration. Typically, the area of these strips 12 is at least about one square inch, and usually is from about 1 to 5 square inches.

Figure 2:
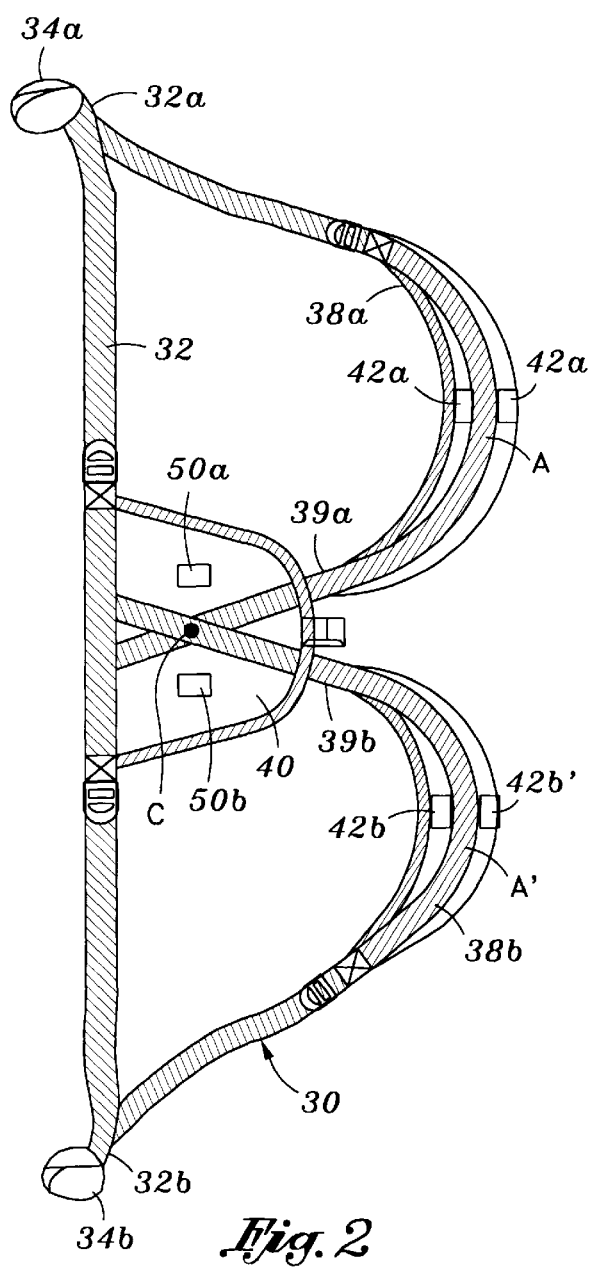
FIG. 2 is a perspective view of a dual looped strap that is adapted to be connected to a golf bag.

FIG. 2 depicts a dual loop strap 30 that has an elongated bridging member 32 with clips 34a and 34b at opposed ends 32a and 32b thereof that are adapted to be detachably connected to rings on a golf bag. For example, this strap 30 may be connected by the clips 34a and 34b respectively to the rings 36a and 36b on the golf bag 10. There are a pair of loop members 38a and 38b which have their inward ends 39a and 39b connected to a back pad 40 that is centrally located along the elongated bridging member 32. The outer ends 39c and 39d of the loop members 38a and 38b are respectively connected to the opposed ends 32a and 32b of the bridging member 32.

In accordance with this invention, there are magnetic strips 42a,42a' and 42b, 42b' respectively embedded in each loop member 38a and 38b at the apexes A and A'. The pairs of strips 42a and 42a' are side by side in the loop member 38a and the pairs of strips 42b and 42b' 42a' are side by side in the loop member 38a. The user's shoulders make contact with these apexes A and A' when the loop members 38a and 38b are draped over the shoulders when carrying a golf bag to bring the magnetic strips 42a and 42b into close proximity with the user's shoulders. Also in accordance with this invention, there are magnetic strips 50a and 50b embedded in the back pad 40. When the strapped is connected to a golf bag being carried by a user with the strap 30 draped over the shoulders, these magnetic strips 50a and 50b come into close proximity with the user's lower back. With the magnetic strips 50a and 50b positioned centrally on either side of the center C of the back pad 40, one strip 50a will be on one side of the user's back bone and the other strip 50b will be on the other side of the user's back bone.

In both embodiments of this invention, the golf bag 10 and the strap 30, when in use as discussed above, the magnetic strips 12, 42a, 42a', 42b, 42b', and 50a and 50b are in close proximity to the portion of the user's body that may be experiencing pain to generate a magnetic field that penetrates the user's body next to these magnetic strips to assist in easing any pain being experienced in the vicinity of the strips. Preferably, all these magnetic strips 12, 42a, 42a', 42b, 42b', and 50a and 50b are flexible, particularly strips 42a, 42a', 42b, 42b' in the shoulder loops 38a and 38b. Suitable flexible magnetic strips may be purchased from Magnet Sales & Manufacturing, Inc. of Culver City, Calif.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiment disclosed. On the contrary, the intention is to cover all modifications and alternate constructions coming within the spirit and scope of the invention as generally expressed by the following claims, which particularly point out and distinctly claim the subject matter of the invention.

What is claimed is:

1. A golf bag comprising a bag body including a sidewall and having a cavity therein adapted to hold golf clubs, and a shoulder strap connected to the sidewall and adapted to be draped over a shoulder of a user, said shoulder strap having magnetic material therein in the form of a flexible strip.

2. The golf bag of claim 1 where the sidewall has magnetic material attached thereto.

3. The golf bag of claim 1 where the shoulder strap has a pair of loops and a back pad that is positioned next to the back of a user when the user carries the golf bag with the shoulder strap draped over both shoulders, said back pad including magnetic material.

4. A golf bag comprising a bag body including a sidewall and having a cavity therein adapted to hold golf clubs, and a shoulder strap connected to the sidewall and adapted to be draped over a shoulder of a user, said sidewall has magnetic material therein in the form of a flexible strip.

5. The golf bag of claim 4 where the sidewall includes a back pad that is positioned next to the back of a user when the user carries the golf bag, said back pad including magnetic material.

6. A strap adapted to be attached to a golf bag including an elongated member having connector members at opposed ends thereof, and magnetic material in the form of a flexible strip attached to the elongated member that is positioned to make contact with the body of a person carrying a golf bag by draping over the person's shoulder the elongated member that is attached to the golf bag.

7. A method of treating pain while playing golf comprising carrying a golf bag with magnetic material included in a portion of the golf bag that is positioned next to the area of the user's body experiencing pain as the golf bag is carried.

8. The method of claim 7 where the portion of the golf bag including the magnetic material is a stap draped over the shoulder.

9. The method of claim 8 where the shoulder strap has a pair of loops and a back pad that is positioned next to the back of a user as the user carries the golf bag with the shoulder strap draped over both shoulders, said back pad including magnetic material.

10. The method of claim 7 where the portion of the golf bag including the magnetic material is a sidewall of the golf bag making contact with the user's back as the golf bag is carried.

11. The method of claim 10 where the sidewall includes a back pad that is positioned next to the back of a user as the user carries the golf bag, said back pad includes the magnetic material.

* * * * *